(12) United States Patent
Ananda Yogendran (10) Patent No.: US 9,153,024 B2
(45) Date of Patent: Oct. 6, 2015

(54) METHOD AND SYSTEM FOR PREDICTING SPATIAL AND TEMPORAL DISTRIBUTIONS OF THERAPEUTIC SUBSTANCE CARRIERS

(71) Applicant: CRIXlabs, Inc., San Francisco, CA (US)

(72) Inventor: Shalini Ananda Yogendran, San Francisco, CA (US)

(73) Assignee: CRIXlabs, Inc., San Francisco, CA (US)

( * ) Notice: Subject to any disclaimer, the term of this patent is extended or adjusted under 35 U.S.C. 154(b) by 0 days.

(21) Appl. No.: 14/449,852

(22) Filed: Aug. 1, 2014

(65) Prior Publication Data
US 2015/0036889 A1   Feb. 5, 2015

Related U.S. Application Data (60) Provisional application No. 61/861,825, filed on Aug. 2, 2013.

(51) Int. Cl.
  *G06T 7/00*       (2006.01)
  *G06F 19/00*      (2011.01)
  *A61B 5/00*       (2006.01)

(52) U.S. Cl.
  CPC ............ *G06T 7/0016* (2013.01); *A61B 5/4848* (2013.01); *G06F 19/706* (2013.01); *G01N 2500/00* (2013.01); *G01N 2800/52* (2013.01); *G06T 2207/10061* (2013.01); *G06T 2207/20081* (2013.01); *G06T 2207/30104* (2013.01)

(58) Field of Classification Search
  CPC ... G06T 7/0016; G06T 7/0012; G06T 3/0087; G06T 7/0032; G06T 7/0036; G06T 2207/10061; G06T 2207/20081; G06T 2207/30024; G06T 2207/30101; G01N 2500/00; G01N 2550/00; G01N 2800/52; G01N 2800/709; G06F 19/706; G06F 19/707; A61B 5/4836; A61B 5/4839; A61B 5/4848
  See application file for complete search history.

(56) References Cited

U.S. PATENT DOCUMENTS

| | | | | |
|---|---|---|---|---|
| 5,919,646 A | * | 7/1999 | Okun et al. | 506/10 |
| 5,932,872 A | * | 8/1999 | Price | 250/201.3 |
| 5,991,028 A | * | 11/1999 | Cabib et al. | 356/456 |
| 6,083,763 A | * | 7/2000 | Balch | 506/9 |
| 6,103,479 A | * | 8/2000 | Taylor | 506/14 |
| 6,222,093 B1 | * | 4/2001 | Marton et al. | 800/3 |
| 6,345,115 B1 | * | 2/2002 | Ramm et al. | 382/133 |
| 6,402,689 B1 | * | 6/2002 | Scarantino et al. | 600/300 |
| 6,542,858 B1 | | 4/2003 | Grass et al. | |

(Continued)

*Primary Examiner* — Manav Seth
(74) *Attorney, Agent, or Firm* — Cooley LLP (57) ABSTRACT

A method and system for predicting spatial and temporal distributions of therapeutic substance carriers within a body of a user, comprising: at a computing system, receiving an image dataset and a spectra dataset of a therapeutic substance carrier generated from at least one of an imaging model and a spectra-generating module; transforming the image dataset and the spectra dataset into a set of characteristics, wherein the set of characteristics comprises electrotopological characteristics and geometrical characteristics; generating a set of pharmacokinetic parameters and a set of pharmacodynamic parameters for the therapeutic substance carrier based upon the set of characteristics and a transformation model; and transforming the set of pharmacokinetic parameters and the set of pharmacodynamic parameters into a spatial distribution and a temporal profile of the therapeutic substance carrier, based upon a predictive model incorporating physiological parameters of the body, thereby predicting distributions of the therapeutic substance carrier within the body.

20 Claims, 4 Drawing Sheets

(56) References Cited

U.S. PATENT DOCUMENTS

| | | | |
|---|---|---|---|
| 6,573,063 B2* | 6/2003 | Hochman | 435/29 |
| 6,615,141 B1* | 9/2003 | Sabry et al. | 702/19 |
| 6,738,716 B1* | 5/2004 | Sabry et al. | 702/19 |
| 6,919,376 B2 | 7/2005 | Llompart et al. | |
| 6,963,770 B2* | 11/2005 | Scarantino et al. | 600/436 |
| 6,963,771 B2* | 11/2005 | Scarantino et al. | 600/436 |
| 8,088,785 B2 | 1/2012 | Llompart et al. | |
| 8,148,414 B2* | 4/2012 | Gangakhedkar et al. | 514/376 |
| 8,346,347 B2 | 1/2013 | Altshuler et al. | |
| 8,540,664 B2 | 9/2013 | Robertson et al. | |
| 2002/0055092 A1* | 5/2002 | Hochman | 435/4 |
| 2002/0137991 A1* | 9/2002 | Scarantino et al. | 600/300 |
| 2003/0130797 A1 | 7/2003 | Skolnick et al. | |
| 2003/0215877 A1 | 11/2003 | Love et al. | |
| 2005/0074803 A1 | 4/2005 | Schmitt et al. | |
| 2005/0089923 A9 | 4/2005 | Levinson et al. | |
| 2006/0282236 A1 | 12/2006 | Wistmuller | |
| 2011/0144525 A1 | 6/2011 | Megej et al. | |
| 2013/0115271 A1 | 5/2013 | Zamboni et al. | |
| 2013/0329973 A1* | 12/2013 | Cao et al. | 382/128 |

* cited by examiner

METHOD AND SYSTEM FOR PREDICTING SPATIAL AND TEMPORAL DISTRIBUTIONS OF THERAPEUTIC SUBSTANCE CARRIERS

CROSS-REFERENCE TO RELATED APPLICATIONS

This application claims the benefit of U.S. Provisional Application Ser. No. 61/861,825 filed 2 Aug. 2013, which is incorporated in its entirety herein by this reference.

TECHNICAL FIELD

This invention relates generally to the therapeutic substance delivery field, and more specifically to a new and useful method for predicting spatial and temporal distributions of a therapeutic substance carriers.

BACKGROUND

Pharmacokinetics is the study of the time course of a drug within the body, based upon absorption, distribution, metabolism, excretion (i.e., ADMET properties), as well as other properties. For a nanotherapeutic to be effective, it must have certain pharmacodynamic and/or pharmacokinetic properties so that it can sufficiently inhibit or modulate a disease process. Drug discovery processes are typically lengthy and costly, spanning an average of 13 years in the United States, and averaging over 800 million dollars in development costs. Typically, pharmacodynamic and/or pharmacokinetic properties of a drug are evaluated experimentally, in vivo and in vitro, during pre-clinical and clinical phases of development; however, approximately 60% of potential drugs fail at this stage, and over half of these failures can be attributed to deficient pharmacodynamic and/or pharmacokinetic properties. While models exist to analyze pharmacodynamic and/or pharmacokinetic properties of a therapeutic substance carrier (e.g., drug or drug carrier, cosmeceutical active, other active, etc.), current models have limited accuracy, cannot be generalized to a wide variety of drug types, are computationally expensive, and are insufficient for many other reasons.

Thus, there is a need in the therapeutic substance delivery field for a new and useful method for predicting spatial and temporal distributions of therapeutic substance carriers. This invention provides such a new and useful method.

DESCRIPTION OF THE PREFERRED EMBODIMENTS

The following description of preferred embodiments of the invention is not intended to limit the invention to these preferred embodiments, but rather to enable any person skilled in the art to make and use this invention.

1. Method

Figure 1A:
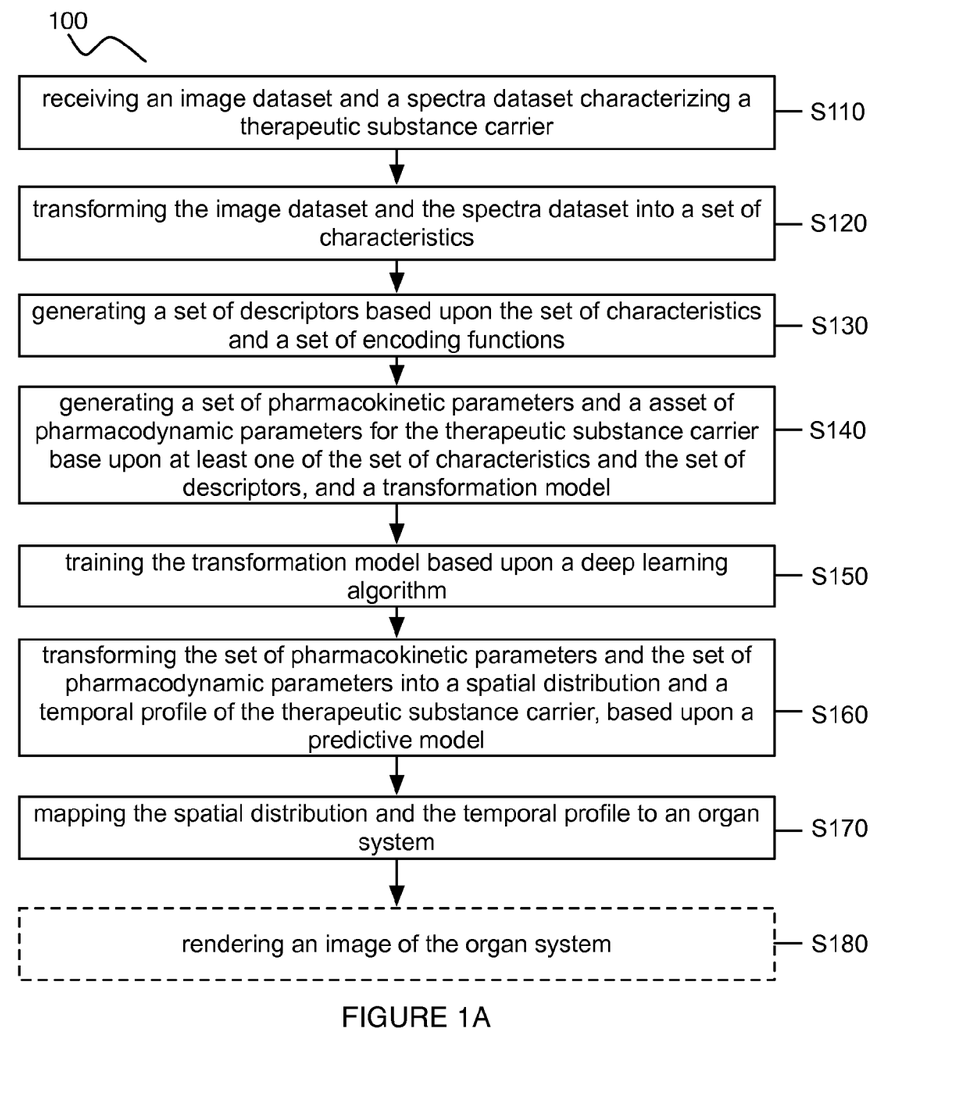
FIGS. 1A and 1B depict schematics of an embodiment of a method for predicting spatial and temporal distributions of therapeutic substance carriers.
Figure 1B:
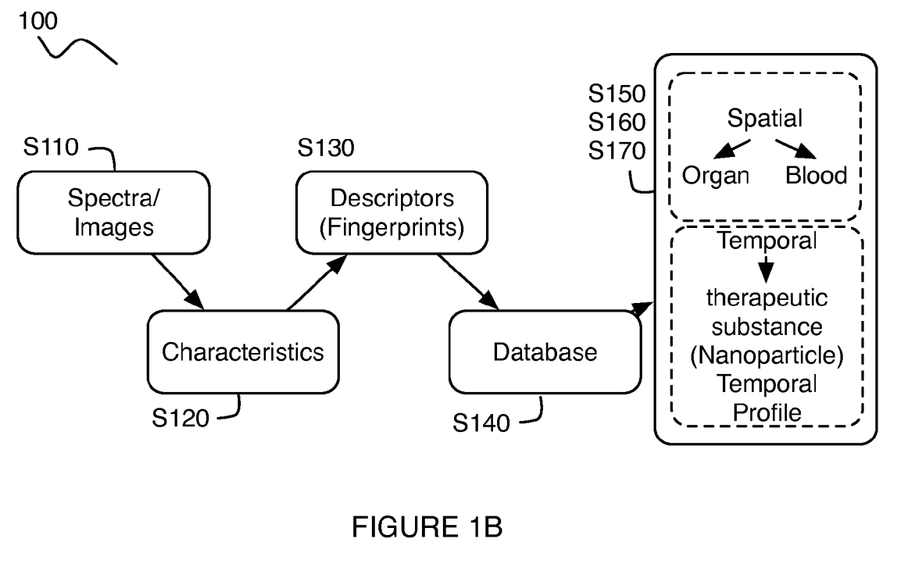

As shown in FIGS. 1A and 1B, an embodiment of a method 100 for predicting spatial and temporal distributions of therapeutic substance carriers comprises: receiving an image dataset and a spectra dataset characterizing a therapeutic substance carrier S110; transforming the image dataset and the spectra dataset into a set of characteristics, wherein the set of characteristics comprises electrotopological characteristics, connectivity characteristics, molecular characteristics, and geometrical characteristics S120, generating a set of descriptors based upon the set of characteristics and a set of encoding functions S130, generating a set of pharmacokinetic parameters and a set of pharmacodynamics parameters for the therapeutic substance carrier based upon at least one of the set of characteristics and the set of descriptors, and a transformation model S140, training the transformation model based upon a deep learning algorithm S150, transforming the set of pharmacokinetic parameters and the set of pharmacodynamic parameters into a spatial distribution and a temporal profile of the therapeutic substance carrier, based upon a predictive model S150; and mapping the spatial distribution and the temporal profile to an organ system, thereby characterizing at least one of a concentration of the therapeutic substance carrier and a concentration of a therapeutic substance carried by the therapeutic substance carrier in the organ system within a time window S170. The method 100 can further comprise rendering an image of the organ system mapped with at least one of the concentration of the therapeutic substance carrier, the concentration of the therapeutic substance, the spatial distribution, and the temporal profile S180.

The method 100 functions to provide an accurate and comprehensive model of a spatial distribution and a temporal profile of a therapeutic substance carrier/therapeutic substance within a patient's body, based upon physical and chemical characteristics of the therapeutic substance carrier/therapeutic substance extracted from data, as well as physiologically based pharmacokinetic (PBPK) models. As such, the method 100 can be used as a tool for accurately predicting the pharmacokinetic and/or pharmacodynamic properties of a therapeutic substance particle (e.g., drug, drug carrier, cosmeceutical active, other active, etc.), as well as the behavior of the therapeutic substance particle within a patient's body, which substantially reduces costs and prevents failure during therapeutic substance development. In some variations, the method 100 can provide a holistic or global view of therapeutic substance particle behavior within a patient's entire body; however, in other variations, the method 100 can provide a more localized view of therapeutic substance behavior within a portion of a patient's body. Preferably, the method 100 is generalizeable to accommodate a wide variety of therapeutic substance types and a wide spectrum of patients; however, the method 100 can target any suitable range of therapeutic substance and/or patient types.

In one application, the method 100 can be used to characterize and model therapeutic substance carriers with lengths in two or three dimensions between 1 nanometer and 1 micrometer, and can produce biodistribution and half-life predictions of these drug carriers within a patient's body based upon input physical and chemical characteristics derived from image data, spectra data, and/or any other suitable type of data. In variations of this application, a spatial and temporal profile of a therapeutic substance carrier can be generated based upon an embodiment of the method 100, wherein the spatial and temporal profile are generated for all or a subset of body organs/body systems of a patient who receives the therapeutic substance carrier by direct injection into the bloodstream, inhalation, application through skin, and/or any other suitable method of delivering a therapeutic substance carrier/therapeutic substance to a patient. In other applications, the method 100 can be used to characterize any other suitable particles of any other suitable dimension(s) and of any suitable composition, and can produce predictions of a distribution of any other suitable parameter within any other system.

Block S110 recites: receiving an image dataset and a spectra dataset characterizing the therapeutic substance carrier, and functions to provide a data source for extracting physical and chemical characteristics of the therapeutic substance carrier. The image dataset is preferably received from a microscopy imaging module, but can additionally or alternatively be received from any other suitable imaging module. In variations, the image dataset can be received from one or more of: a scanning electron microscopy (SEM) module, a transmission electron microscopy (TEM) module, an atomic force microscopy (AFM) module, a helium ion microscopy (HIM) module, and any other suitable module. The spectra dataset is preferably received from a spectroscopy and/or a spectrometry module, but can additionally or alternatively be received from any other suitable module. In variations, the spectra dataset can be received from one or more of a Fourier transform infrared spectroscopy (FTIR) module, a nuclear magnetic resonance (NMR) spectroscopy module, a mass spectrometry (MS) module, and any other suitable module. The image dataset and the spectra dataset are preferably received at a processor configured to transform the datasets into a set of characteristics in Block S120; however, the image dataset and the spectra dataset can be received at any other suitable data receiving element and/or processing element.

In Block S110, the therapeutic substance carrier is preferably a molecular composition configured to facilitate delivery of a therapeutic substance to a desired target of the user's body, wherein delivery is intended to be performed orally, by injection, by application to the user's skin, and/or in any other suitable manner. In some variations, the therapeutic substance carrier characterized by the image and spectra datasets can comprise a coupled therapeutic substance for delivery into the user's body. In other variations, the therapeutic substance carrier can comprise a molecular substrate separate from but configured to bind to an active therapeutic compound or class of active therapeutic compounds (e.g., active substance, active group), such that analyses generated from datasets characterizing the molecular substrate can be generalized to classes of therapeutic compounds.

In some variations, the image dataset and/or the spectra dataset of Block S120 can be received directly from the microscopy imaging module and/or the spectroscopy/spectrometry module. However, the image dataset and/or the spectra dataset can additionally or alternatively be received from a storage module of a computing system in communication with any one or more of the microscopy imaging module, the spectroscopy module, and the spectrometry module.

Figure 2:
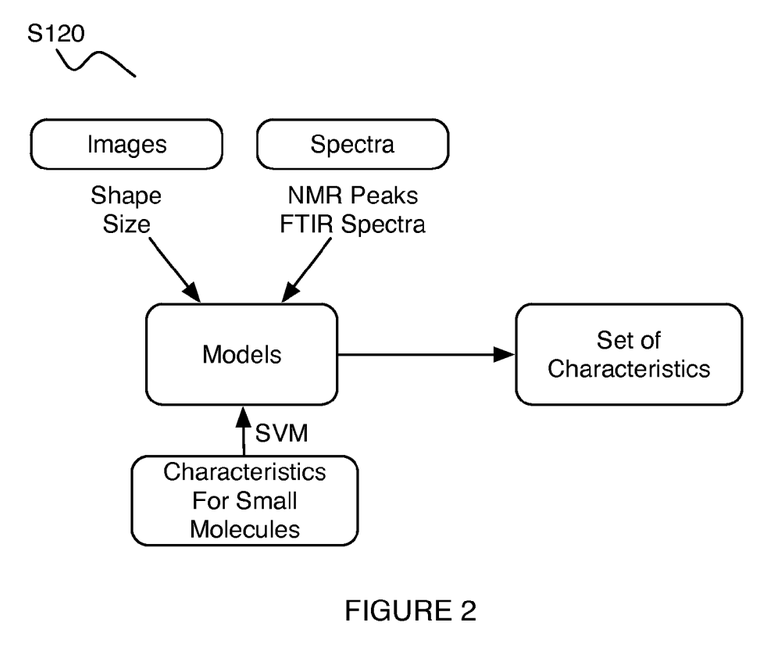
FIG. 2 depicts a portion of an embodiment of a method for predicting spatial and temporal distributions of therapeutic substance carriers.

Block S120 recites: transforming the image dataset and the spectra dataset into a set of characteristics, and as shown in FIG. 2, which functions to generate a set of physical and chemical characteristics of the therapeutic substance carrier from the datasets received in an embodiment of Block S110. Transforming the image dataset and the spectra dataset is preferably performed at a processing subsystem that receives the image and the spectra datasets; however, transforming the image dataset and/or the spectra dataset can alternatively be performed at any other suitable processing subsystem. In some variations, the processing subsystem configured to transform the image dataset and the spectra dataset into a set of characteristics, as in Block S120, can comprise a single processor or any suitable number of processors.

Transforming the image dataset in Block S120 can comprise implementing an edge fidelity-improving stage (e.g. on an object of the image dataset) comprising any one or more of: an edge-preserving image mechanism, an automatic segmentation method, an object reconstruction algorithm, a classification method, a geometry-driven scheme, and any other edge-processing method. Transforming the image dataset can additionally or alternatively comprise any suitable denoising and/or shape-extraction stage. In one variation, transforming the image dataset comprises image analysis based upon a geometric model that relies upon estimating motion(s) of curves and surfaces of a particle that moves in a normal direction at a given speed. In one example of the geometric model, given a surface x that is moving under a speed $F(x)$, a level set equation can be generated to represent once-at-a-time search (OTS) motion for the particle. In the example, the surface x can be embedded as the zero level set of a higher dimensional function, and used to generate an equation of motion for the surface and/or the particle. In the example, the zero level set of the higher dimensional function can change topology and form sharp corners, the higher dimensional function can implement a discrete grid and finite difference approximations to approximate a solution, the higher dimensional function can be used to extract intrinsic geometric properties (e.g., normal and curvate of curves) of the particle, and solutions can be extended to motion in multiple dimensions. Transforming the image dataset can, however, comprise any other suitable stage(s) configured to facilitate image processing and/or extraction of the set of characteristics.

Transforming the spectra dataset in Block S120 preferably comprises performing a peak and trough analysis, and can additionally or alternatively comprise implementing any one or more of: a denoising stage, a smoothing stage, a scaling stage, an amplification stage, and any other suitable stage for spectra data processing. In one variation, transforming the spectra dataset comprises a peak and trough analysis that enables identification of peaks and troughs, as well as calculations of areas under relevant portions of a spectrum, in order to extract information that can be used to derive the set of characteristics. In one example, transforming the spectra dataset comprises implementing a two-phase algorithm that 1) identifies strategic points by solving a sequence of maximum orthogonal (i.e., Euclidean) distance problems and 2) solves a nonlinear programming problem (NLP) with the strategic points to find optimal line segments constituting a solution to the NLP. In the example, the two-phase algorithm produces a continuous piecewise linear approximation to the raw spectra data, from which maxima (i.e., peaks) and/or minima (i.e., troughs) can be extracted. Furthermore, in the example, identified maxima and minima from the approximation can be used to calculate relevant spectra areas using any suitable method (e.g., by a quadrature rule). Transforming the spectra dataset can, however, comprise implementing any other suitable stage(s) configured to facilitate extraction of the set of characteristics from raw spectra data.

The set of characteristics generated from the image dataset and the spectra dataset in Block S120 preferably comprises electrotopological characteristics, connectivity characteristics, molecular characteristics, and geometrical characteristics, but can additionally or alternatively comprise any other suitable characteristics and/or combination of characteristics that can be used to generate a set of descriptors for a predictive model. The electrotopological characteristics can comprise any one or more of: molecular electrotopological-state (E-state) values (e.g., maximum E-state, minimum E-state), a hydrogen E-state value (e.g., minimum E-state), amino acid E-state values, sums of amino acid E-state values (e.g., sums of aaN atom type, aaNH atom type, and/or daaN atom type E-states), sums of additional E-state values (e.g., sum of ddssS atom type E-states), sums of E-state values for molecular groups or atoms of molecular groups (e.g., sums of hydrogen E-states for all —$NH_2$ groups, —$CH3$ E-states, —F E-states, —OH E-states, —NH— E-states, >C— E-states, >C< E-states), internal hydrogen bonding characteristics (e.g., bonding indices, number of skeletal bonds), and any other suitable electrotopological characteristic. The connectivity characteristics can comprise any suitable chi index or indices (e.g., simple $3^{rd}$ order cluster chi index, simple $7^{th}$ order chain chi index, simple $9^{th}$ order chain chi index, simple $10^{th}$ order chain chi index, valence $5^{th}$ order chain chi index, valence $7^{th}$ order chain chi index, valence $9^{th}$ order chain chi index). The molecular characteristics can comprise any one or more of: counts of groups (e.g., aaN type groups, aaNH type groups, —$CH_2$— groups, >N— groups, etc.) in a molecule, number of chemical elements in a molecule, polarity indices, charge characteristics (e.g., larges and smallest negative charges), ovality, and any other suitable molecular characteristic. The set of geometrical characteristics can comprise any one or more of: displacement components between center-of-mass and center-of-dipole along an inertial axis for the carrier, principal moments of inertia for the carrier, dipole components along an inertial axis for the carrier, magnitudes of quadrupole moments for the carrier, components of tensors in inertial coordinate frames for the carrier, and any other suitable geometrical characteristic. The set of characteristics can, however, comprise any other suitable physical and/or chemical characteristic.

Figure 3:
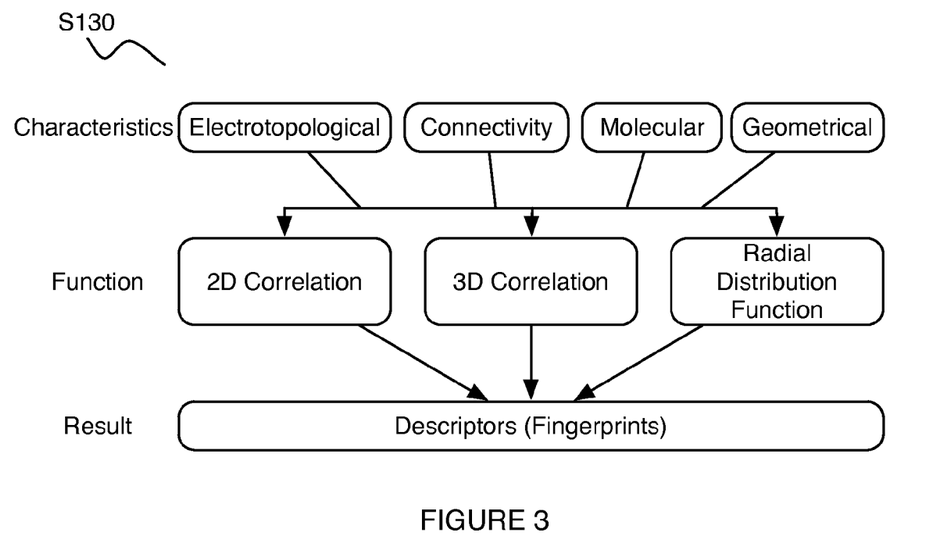
FIG. 3 depicts a portion of an embodiment of a method for predicting spatial and temporal distributions of therapeutic substance carriers.

Block S130 recites: generating a set of descriptors based upon the set of characteristics and a set of encoding functions, and as shown in FIG. 3, functions to define a set of fingerprints that encode the set of characteristics into a reduced number of descriptors from which model inputs are derived. The descriptors are preferably associated with particles (e.g., therapeutic substance carriers) that are delivered by injection, inhalation, and/or transdermal application, but can additionally or alternatively be associated with any other suitable particle that is delivered in any other suitable manner. The set of descriptors generated in Block S130 preferably comprises paired property descriptors comprising combinations of multiple characteristics and/or descriptors, wherein each paired property descriptor has a direct correlation to a spatial distribution and/or temporal profile of an associated particle in a patient's body. The set of descriptors can, however, comprise any single descriptor and/or combination of descriptors based upon the set of characteristics from an embodiment of Block S120.

In one variation, the set of encoding functions for processing the set of characteristics into a set of descriptors comprises one or more of: 2D autocorrelation, 3D autocorrelation, and radial distribution functions; however, in other variations, the set of encoding functions can comprise any other suitable encoding function. Furthermore, any other suitable process can be implemented in variations of Block S130 to transform the set of characteristics into a set of descriptors, from which model inputs are derived. Additionally, implementation of an encoding function can comprise a weighting step, such that a variation of the encoding functions can comprise any one or more of: 2D autocorrelation functions with weighting, 3D autocorrelation functions with weighting, and radial distribution functions with weighting.

In a first example of Block S130, the set of descriptors comprises descriptors including a fingerprint derived from scalar descriptors characterizing the therapeutic substance carrier (e.g., compound molecular weight, number of hydrogen bonding acceptors, number of hydrogen bonding donors, topological polar surface area, octanol/water partition coefficients, total charge of a molecule). The set of descriptors in the example can further comprise a fingerprint derived from any one or more of: a 2D autocorrelation function implemented on aromaticity indices, a Hansch substituent constant, a partition coefficient, and a distribution coefficient; a fingerprint derived from a 2D autocorrelation function implemented on steric parameters (e.g., Charton, Taft), molar refractivity, and parachor; a fingerprint derived from a 2D autocorrelation function implemented on atom-pair values, a Balaban index, BCUT, and information content indices; and a fingerprint derived from a 2D autocorrelation function weighted with van der Waals surface area, implemented on shape indices (e.g., Kappa shape indices, Kier shape indices), connectivity indices, flexibility indices, and charges (e.g., sigma, pi). However, variations of the first example can comprise any other suitable fingerprints derived from scalar descriptors and/or 2D autocorrelation functions with or without weighting.

In variations of the first example, the set of descriptors can additionally or alternatively comprise descriptors including a fingerprint derived from a 3D autocorrelation function implemented on highest occupied molecular orbital (HOMO) and lowest unoccupied molecular orbital (LUMO) energy values, charges, and polarizability metrics; a fingerprint derived from a 3D autocorrelation function implemented on molecular walk and atomic counts; a fingerprint derived from a 3D autocorrelation function implemented on Randic indices; a fingerprint derived from a 3D autocorrelation function implemented on orbital electron densities, superdelocalizabilities, polarizabilities (e.g., atom-atom, molecular), energies, dipole moments, and polarity indices; a fingerprint derived from a 3D autocorrelation function implemented on shadow indices, surface area properties, and electrostatic properties; a fingerprint derived from a 3D autocorrelation function weighted with van der Waals surface area, implemented on a Wiener index, overall shape parameter, and total charge value; and a fingerprint derived from a 3D autocorrelation function weighted with van der Waals surface area, implemented on charge characteristics (e.g., topological indices, maximum and minimum charges), molecular polarizabilities, hydrogen bonding capacities, and charged polar surface area. However, other variations of the first example can comprise any other suitable fingerprints derived from scalar descriptors and/or 3D autocorrelation functions with or without weighting.

In variations of the first example, the set of descriptors can additionally or alternatively comprise descriptors including a fingerprint derived from a radial distribution function weighted and non-weighted with van der Waals surface area, implemented on a gravitation index and molecular characteristics (e.g., surface area, volume, morphology) of the therapeutic substance carrier; a fingerprint derived from a radial distribution function implemented on electrotopological state indices of the therapeutic substance carrier; a fingerprint derived from a radial distribution function, weighted and non-weighted with van der Waals surface area, implemented on a Wiener index of the therapeutic substance carrier, an overall shape parameter for the therapeutic substance carrier, and a total charge of the therapeutic substance carrier; a fingerprint derived from a radial distribution function weighted and non-weighted with van der Waals surface area, implemented on orbital electron densities, superdelocalizabilities, polarizabilities (e.g., atom-atom, molecular), energies, dipole moments, and polarity indices of the therapeutic substance carrier; a fingerprint derived from a radial distribution function weighted with van der Waals surface area and implemented on shape indices, connectivity indices, flexibility indices, and charges of the therapeutic substance carrier; and a fingerprint derived from a radial distribution function implemented on other fingerprints of the set of descriptors. However, other variations of the first example can comprise any other suitable fingerprints derived from radial distribution functions with or without weighting.

Variations of Block S130 can, however, implement encoding functions in addition to and/or other than 2D autocorrelation functions, 3D autocorrelation functions, and/or radial distribution functions.

Block S140 recites: generating a set of pharmacokinetic parameters and a set of pharmacodynamics parameters for the therapeutic substance carrier based upon at least one of the set of characteristics and the set of descriptors, and a transformation model. Block S140 functions to use a model configured to receive an input derived from the set of characteristics/the set of descriptors and to output a set of pharmacokinetic parameters and a set of pharmacodynamic parameters, in order to transform the set of descriptors into a set of parameters that can be used to characterize a spatial distribution and a temporal profile of the therapeutic substance carrier. The set of pharmacokinetic and pharmacodynamic parameters preferably comprises a volume of distribution (Vd) based upon an administered dose normalized to an initial concentration of the therapeutic substance carrier, an unbound volume of distribution based upon Vd normalized by an unbound fraction, a clearance of a therapeutic substance carrier/therapeutic substance from the patient's body, and a half-life of the therapeutic substance carrier/therapeutic substance; however, the set of pharmacokinetic and pharmacodynamic parameters can additionally or alternatively comprise any other suitable parameters that can be used to characterize a spatial distribution and/or a temporal profile of the therapeutic substance carrier.

Figure 4:
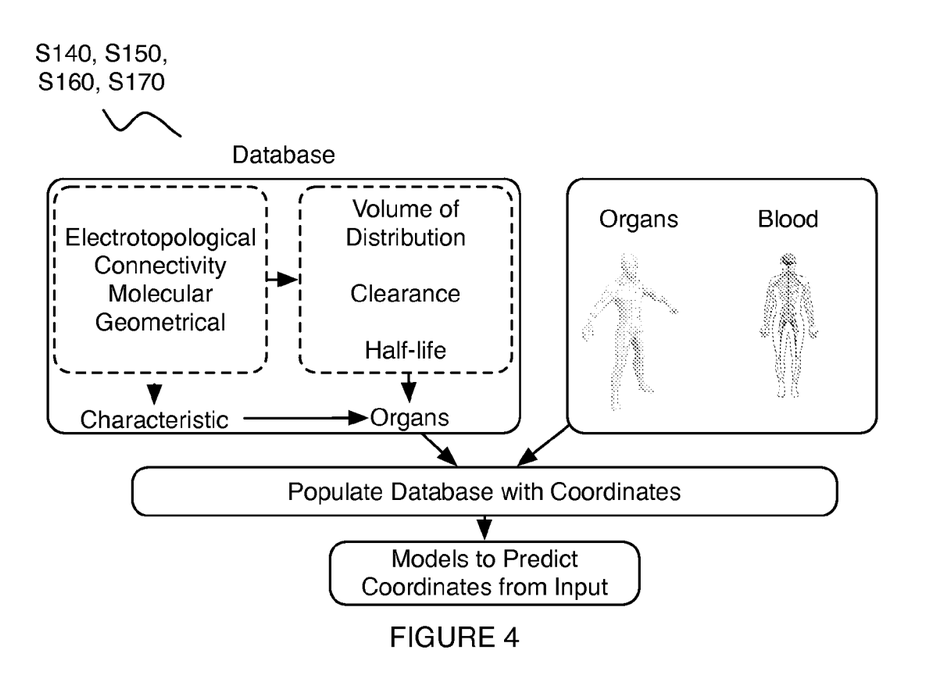
FIG. 4 depicts a portion of an embodiment of a method for predicting spatial and temporal distributions of therapeutic substance carriers.

As shown in FIG. 4, the model of Block S140 is preferably supported by a database procured from the set of characteristics of Block S120, wherein the database preferably comprises quantified values of the set of characteristics of Block S120. The database thus preferably comprises one or more of: quantified values of electrotopological characteristics, quantified values of connectivity characteristics, quantified values of molecular characteristics, and quantified values of geometrical characteristics, and can additionally or alternatively comprise any other suitable quantified values of additional characteristic(s). In an example, the database comprises quantified values of electrotopological characteristics based upon E-states, E-state sums, centric indices, and other suitable indices; quantizations of connectivity characteristics including suitable chi indices; quantizations of molecular characteristics including atom and bond counts; quantizations of quantum chemical characteristics including hydrogen bond donor characteristics, dipole moments, hardness, softness, ionization potential, electron affinity, chemical potential, electronegativity index, electrophilicity index, and charge parameters (e.g., negative and positive charge values for different atoms); and quantizations of geometrical characteristics based upon length vectors, surface areas, (e.g., polar molecular areas, solvent accessible areas, van der Waals areas), rugosity, globularity, hydrophobisicity, capacity, hydrophilicity (e.g., integy moments), and amphiphilicity.

In variations, the database can further serve as a map or decision tree that governs which functions the transformation model implements to process a set of data characterized by inputs of the transformation model. For example, an input that maps to a given quantified value of an electrotopological characterization in the database can govern a function or a set of functions used to process the input (or data associated with the input), mapped to the electrotopological characterization, according to the transformation model. Furthermore, an input that maps to a subset of the quantified characteristics of the database can be processed by multiple functions associated with the characteristics, in sequence and/or simultaneously, according to the transformation model. In other variations, the transformation model can additionally or alternatively be supported by any other suitable database of characteristics, and/or can implement any function(s) that transform an input into a set of pharmacokinetic parameters and a set of pharmacodynamic parameters.

Block S150 recites: training the transformation model based upon a deep learning algorithm, and functions to refine the model based upon a suitable machine learning algorithm, such that the model can be applied to a wide range of particles therapeutic substance carriers (e.g., an entire nanoparticle population).

In one variation of Block S150, the deep learning algorithm is preferably based upon a combinatorial approach that can accommodate networks with a large number of hidden layers, but can be based upon any other suitable approach. Preferably, the combinatorial approach can find a suitable set of parameters efficiently with deep networks comprising millions of parameters and a large number of hidden layers (e.g., the combinatorial approach can implement a greedy learning algorithm), can be applied to labeled data by learning a model that generates both the label and the data, can implement a fine-tuning algorithm that learns a generative model, implements unsupervised learning, and can facilitate efficient and accurate formation of percepts. The combinatorial approach can, however, be configured in any other suitable manner.

In one variation, training based upon a combinatorial approach can comprise boosting and/or bagging (i.e., bootstrapped aggregation). In this variation, bagging uses different subsets of a set of training data with a single learning method. Given a parameter t, bagging draws t random instances from the set of training data with replacement (i.e., using a uniform distribution) and learns the t instances based upon the single learning method. The drawing and learning process is repeated over multiple cycles, and each cycle results in the generation of one "classifier". Upon constructing multiple classifiers by bagging, an analysis of the predictions of the multiple classifiers can be used to refine the predictions of the transformation model. In this variation, boosting is similar to bagging, and additionally tracks a performance of the learning method while concentrating on drawn instances that have not been correctly learned by the learning method. Thus, boosting does not randomly choose the t instances, but favors instances that have not been accurately learned. After multiple processing cycles, a prediction is generated by performing an analysis on predictions of each "classifier" (e.g., by a weighted vote), wherein the weights are proportional to classifier accuracy in prediction.

The learning algorithm in this variation is preferably a greedy learning algorithm, as described earlier, which can construct multi-layer directed networks one layer at a time. By using the greedy learning algorithm, a generative model being implemented can be refined upon each addition of each new layer to a multi-layer directed network. As such, the learning algorithm can be used to construct deep directed nets to become an undirected graphical model. Furthermore, the greedy learning algorithm can be implemented in cooperation with a Markov chain-Monte Carlo system, or any other suitable system.

Other variations of training the model can comprise implementation of multiple (i.e., different) learning methods, with or without weights assigned to each learning method. In one example, drawing of $N^*(<N)$ instances from an N-dimensional set of training data creates an $N^*(<N)$-dimensional random subspace. Drawing S times produces S subspaces for constructing "classifiers". The "classifiers" are then constructed in the random subspaces and aggregated in an integration procedure to refine a prediction. Training the model in Block S150 can, however, comprise any other suitable method of refining a model.

In an example of Block S150, three factors were additionally analyzed, along with a weighting algorithm, to determine the role of each characteristic contributing to the deep learning algorithm used to train the model. The first factor, $d_{neighbor}$, is a difference in the numbers of neighbor-bonded atoms of specific atom types, in relation to the therapeutic substance carrier; the second factor, $d_{ec}$, is a difference in the extended connectivity value for the therapeutic substance carrier, which is based upon an extended connectivity value for an atom in a molecule and a number of connected heavy atoms with the atom, and employs a double rounded extended connectivity; and the third factor, $d_{topology}$, is a difference in topological distances between two close atom pairs of the therapeutic substance carrier, calculated by a Floyd-Warshall algorithm. In other variations and examples, any suitable factor can be analyzed to determine the role of each characteristic contributing to the deep learning algorithm used to train the model.

The set of training data used to train the model preferably comprises data for a set of previously characterized particles of therapeutic substance carriers (e.g., drug-carriers, drugs, cosmeceutical actives, other actives, nanoparticles) that have been validated experimentally and/or empirically. The set of training data is preferably substantially extensive and comprises a wide variety of particles, so as to avoid empirical bias. In one example, the set of training data comprises data for a set of drugs including Acebutolol, Diazepam, Lornoxicam, Praziquantel, Mercaptoethane sulfonic, Progesterone, Acrivast, Methadone, Propiverine, Iprenolol, Ethinylestradiol, Methylprednisolone, Propylthiouraci, Recainam, Antipyriropine Sorivudine, Bromaz, Bupropi, Granisetron, Nisoldipine, Sulindac, Diclofenac, Meloxicam, Prazosin, Salicylic acid, Dihydrocodeine, Ethambutol, Methotrexate, Propranolol, Aminopyrine, Famciclovir, Metoprolol, Quinidine, Felodipine, Mexiletine, Amrinone, Fenclofenac, Morphine, Flecainide, Moxonidine, Salicylic acid, Fluconazole, Naloxone, Betaxolol, Flumazenil, Naproxen, Sotalol, Fluvastatin, Nefazodone, Spironolactone, Bumetanide, Gallopamil, Nicotine Stavudine, Glyburide, Nicotinic acid, and Sudoxicam. In other examples and variations, however, the set of training data can comprise data for any other suitable set of particles.

Any or all of Blocks S120-S150 can additionally or alternatively implement a machine learning algorithm for the transformation model, and variations, the machine learning algorithm can be characterized by a learning style including any one or more of: supervised learning (e.g., using logistic regression, using back propagation neural networks), unsupervised learning (e.g., using an Apriori algorithm, using K-means clustering), semi-supervised learning, reinforcement learning (e.g., using a Q-learning algorithm, using temporal difference learning), and any other suitable learning style. Furthermore, the machine learning algorithm can implement any one or more of: a regression algorithm (e.g., ordinary least squares, logistic regression, stepwise regression, multivariate adaptive regression splines, locally estimated scatterplot smoothing, etc.), an instance-based method (e.g., k-nearest neighbor, learning vector quantization, self-organizing map, etc.), a regularization method (e.g., ridge regression, least absolute shrinkage and selection operator, elastic net, etc.), a decision tree learning method (e.g., classification and regression tree, iterative dichotomiser 3, $C_{4.5}$, chi-squared automatic interaction detection, decision stump, random forest, multivariate adaptive regression splines, gradient boosting machines, etc.), a Bayesian method (e.g., naïve Bayes, averaged one-dependence estimators, Bayesian belief network, etc.), a kernel method (e.g., a support vector machine, a radial basis function, a linear discriminate analysis, etc.), a clustering method (e.g., k-means clustering, expectation maximization, etc.), an associated rule learning algorithm (e.g., an Apriori algorithm, an Eclat algorithm, etc.), an artificial neural network model (e.g., a Perceptron method, a back-propagation method, a Hopfield network method, a self-organizing map method, a learning vector quantization method, etc.), a deep learning algorithm (e.g., a restricted Boltzmann machine, a deep belief network method, a convolution network method, a stacked auto-encoder method, etc.), a dimensionality reduction method (e.g., principal component analysis, partial lest squares regression, Sammon mapping, multidimensional scaling, projection pursuit, etc.), an ensemble method (e.g., boosting, boostrapped aggregation, AdaBoost, stacked generalization, gradient boosting machine method, random forest method, etc.), and any suitable form of machine learning algorithm.

Block S160 recites: transforming the set of pharmacokinetic parameters and the set of pharmacodynamic parameters into a spatial distribution and a temporal profile of the therapeutic substance carrier, based upon a predictive model. Block S160 functions to use a predictive model, characterizing a spatial distribution and a temporal profile of the therapeutic substance carrier, in order to create a spatial distribution and a temporal profile of the therapeutic substance carrier that can be mapped to a patient's organ systems and/or any other suitable portion of a patient's body. The spatial distribution is preferably generated in a manner that can be mapped to a 2D and/or a 3D model of a portion or the entirety of the patient's body, and is preferably generated based upon the transformation model of Block S140, as trained in Block S150. The temporal profile is preferably based upon the transformation model of Block S140 as trained in Block S150, in cooperation with a probabilistic model to allow generation of a profile of an amount (e.g., concentration, enumeration, density, etc.) of the therapeutic substance carrier within a patient's body over time. Preferably, the probabilistic model comprises a hidden Markov model; however, the probabilistic model can alternatively comprise any other suitable model for generating a temporal profile of the therapeutic substance carrier.

Block S170 recites: mapping the spatial distribution and the temporal profile to an organ system, thereby characterizing at least one of a concentration of the therapeutic substance carrier and a concentration of a therapeutic substance carried by the therapeutic substance carrier in the organ system within a time window S170. Block S170 functions to adapt the spatial distribution and the temporal profile generated in Block S160 to at least a portion of a patient's body, such that the distribution and profile can be used to provide insight into the pharmacological behavior of the therapeutic substance carrier and/or therapeutic substance within the patient's body. In Block S170, the spatial distribution and the temporal profile are preferably mapped to an entire organ system of the patient, thus providing a whole-body analysis of therapeutic substance carrier/therapeutic substance concentrations; however, the spatial distribution and the temporal profile can alternatively be mapped to individual portions of the patient's body, such as individual organ systems, individual tissue structures, and/or any other suitable portion of the patient's body. The organ system or other portion of the patient's body is preferably segmented from an image (e.g., computed tomography image, magnetic resonance image, x-ray image, etc.) or mesh (e.g., finite element model mesh) characterizing the body/body portion, but can alternatively be adapted in any other suitable manner from a model of the patient's body.

In a first example of Block S170, as shown in FIG. 4, a spatial distribution is mapped to an entire organ system of a patient. In the first example, the patient's entire body was divided into grid elements of dimensions 1000×1000×1000, wherein each organ in the body is given its own coordinate system. A topology discovery algorithm was then implemented, wherein each point on a grid in the example corresponded to a pixel, and wherein a pixel was coupled with an empirical distribution value of intensities (e.g., corresponding to a concentration of a nanoparticle). A comparison between two intensities, comprising a correlation between two pixels, was then used to determine if pixels were neighboring or non-neighboring. In the example, the correlation comprised an empirical correlation $p_{ij}$ between the intensity of pixel i and the intensity of pixel j within a defined interval (e.g., $[-1, 1]$). The first example further used an absolute value of the correlation, such that edge effects were accounted for. After generation of a set of absolute correlations, comprising a correlation for each pixel i-pixel j pair, the set of absolute correlations was then converted into a grid with intensities that corresponded to a concentration of particles (e.g., of the therapeutic substance carrier) within the grid, wherein each grid location comprised embedding coordinates. The grid of data vectors was then transformed by 1) defining orthogonal axes and 2) transforming an input of intensities (along with pixel coordinates) into an ordinary discrete image on a grid. The output of this step was then transformed (i.e., scaled, rotated, convolved) and mapped onto the coordinates of corresponding organs of the patient's body.

In a second example of Block S170, as shown in FIG. 4, a spatial distribution was mapped to a patient's vascular system to characterize a distribution and temporal profile of drug carriers in a patient's vascular system. In the second example, the surface area of a patient's entire vascular system was segmented from a computed tomography image and enhanced by application of a line-filter based upon a combination of eigenvalues of a Hessian matrix, thus accentuating blood vessels in relation to other features. Furthermore, initial segmentation comprised thresholding of the line-filter output and specifying a tracking algorithm to fill any voids and/or discontinuities between segments. Additionally, a thinning algorithm was applied to determine branchpoints of the blood vessels, in order to further eliminate non-blood vessel structures. Similar to the first example, a topology discovery algorithm was then applied to the blood vessel model, in order to characterize particle concentrations (e.g., of the therapeutic substance) within the user's blood vessels.

In a third example of Block S170, release of a native drug from a drug carrier, delivered transdermally in a gel formulation, was characterized. In the third example, a generalized distance function method was applied for optimization and an amount of ethanol and an amount of MET were chosen as causal factors. A rate of penetration, a lag time, and a total irritation score were selected as response variables. A set of data of causal factors and response variables was used as training data for an artificial neural network (ANN) model implementing a deep learning algorithm. In the third example, integration of the ANN model with genetic algorithms formed a loop based upon a prediction function of the ANN model and an exploitation function of the genetic algorithms. The ANN model predicted output response variables, based upon new inputs generated by the genetic algorithms, which were compared with target output responses. The looping process was repeated to optimize response variable values, which were then used to optimize the gel formulation design. An optimized gel formulation design was then prepared and evaluated experimentally. Experimentally observed results for the response variables of the optimized gel formulation agreed well with the predicted results from the ANN model.

In some variations, Block S170 further comprises validating an outcome of the predictive model. In one variation, validation can be based upon a receiver operating characteristic (ROC) curve of the predictive model (e.g., an area above the ROC curve), a number of molecules of a therapeutic substance evaluated, a proportion of active compounds in an original set of compounds, and a number of compounds created and evaluated by the predictive model. In the first, second, and third examples of Block S170, an ROC metric of 0.94-0.87 was observed, wherein a metric value of 1 indicates a perfect test, and a metric value of 0.5 indicates a worthless test. Block S170 can, however, comprise validating an outcome of the predictive model in any other suitable manner.

As shown in FIG. 1A, the method 100 can further comprise Block S180, which recites: rendering an image of the organ system mapped with at least one of the concentration of the therapeutic substance carrier, the concentration of the therapeutic substance, the spatial distribution, and the temporal profile. Block S180 functions to transform an output of any block of the method 100 into an image rendering that can visually inform an entity of the pharmacological behavior of the therapeutic substance carrier/therapeutic substance. The image can comprise a still image that displays a relevant distribution parameter, and/or can comprise a video image that displays temporal variations of a relevant distribution parameter. The image can be rendered at a user interface, (e.g., of a mobile device, of a computing device, of a wearable electronic device, of a model of the user comprising electronic display elements, etc.), or at any other suitable interface accessible by the entity.

The method 100 can further comprise any other suitable block(s) or step(s) configured to facilitate reception of image and spectra datasets, processing of image and spectra datasets, generating of inputs for models implementing machine learning algorithms, extracting outputs of models, mapping derivations of outputs on any suitable system to characterize relevant spatial distributions and/or temporal profiles, and providing information derived from the models and to any suitable entity.

As a person skilled in the field of nanomedicine will recognize from the previous detailed description and from the figures and claims, modifications and changes can be made to the preferred embodiments of the method 100 without departing from the scope of the method 100.

2. System

Figure 5:
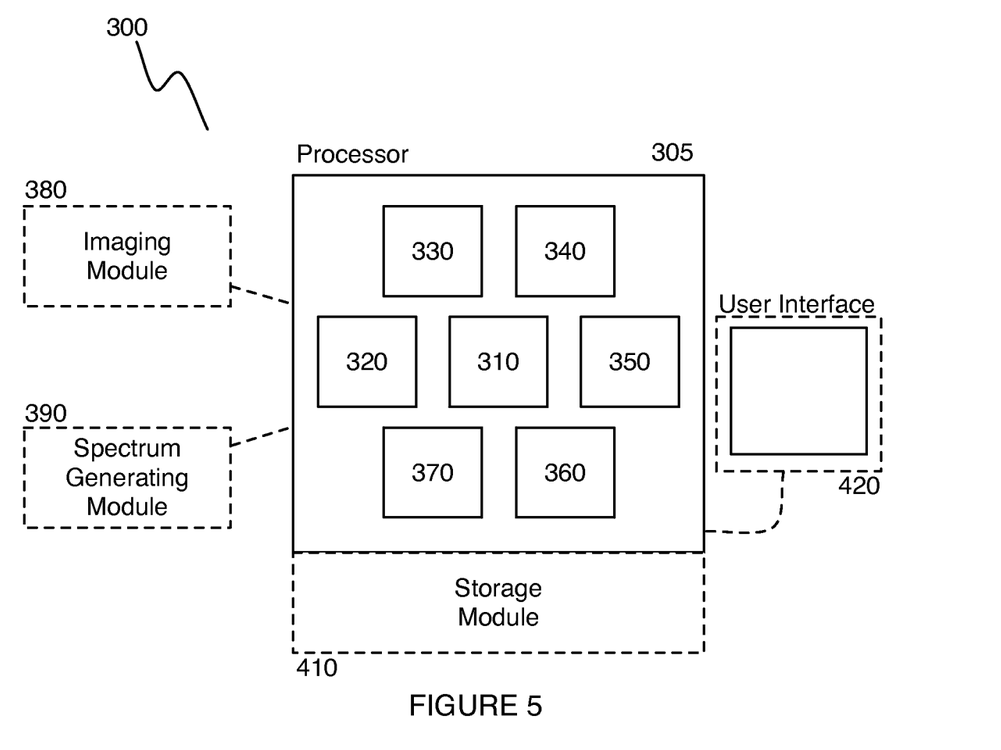
FIG. 5 depicts a schematic of an embodiment of a system for predicting spatial and temporal distributions of therapeutic substance carriers.

As shown in FIG. 5, an embodiment of a system 300 for predicting spatial and temporal distribution of therapeutic substance carriers comprises: a processor 305 comprising a first module 310 configured to receive an image dataset and a spectra dataset characterizing a therapeutic substance carrier, a second module 320 configured to transforming the image dataset and the spectra dataset into a set of characteristics, a third module 330 configured to generate a set of descriptors based upon the set of characteristics and a set of encoding functions, a fourth module 340 configured to form a model configured to receive an input derived from the set of descriptors and output a set of pharmacokinetic parameters and a set of pharmacodynamic parameters, a fifth module 350 configured to train the model based upon a deep learning algorithm, a sixth module 360 configured to generate a predictive model, characterizing a spatial distribution and a temporal profile of the therapeutic substance carrier, based upon the model, and a seventh module configured to map the spatial distribution and the temporal profile to an organ system.

The system 300 can further comprise and/or be configured to couple to an imaging module 380 (e.g., an SEM module, a TEM module, an AFM module, a HIM module), and can further comprise and/or be configured to couple to a spectrum generating module 390 (e.g., an FTIR module, an NRM module, a MS module). In some variations, the system 300 can further comprise a storage module 410 configured to store any one or more of: a database, an input, an output, a prediction, and any suitable data relevant to predicting spatial and temporal distribution of therapeutic substance carriers. Additionally, in variations, the system 100 can further comprise a user interface 420 configured to rendering an image of the organ system mapped with at least one of a concentration of the therapeutic substance carrier, a concentration of the therapeutic substance, a spatial distribution, and the temporal profile to a user or other entity.

The system 300 functions to provide an accurate and comprehensive model of a spatial distribution and a temporal profile of a therapeutic substance carrier/therapeutic substance within a patient's body, based upon physical and chemical characteristics of the therapeutic substance carrier/therapeutic substance extracted from data, as well as physiologically based pharmacokinetic (PBPK) models. As such, the system 300 is preferably configured to implement at least a portion of the method 100 described in Section 1 above; however, the system 300 can additionally or alternatively be configured to implement any other suitable method 100 for predicting spatial and temporal distributions of therapeutic substance carriers.

The method 100 and system 300 of the preferred embodiment and variations thereof can be embodied and/or implemented at least in part as a machine configured to receive a computer-readable medium storing computer-readable instructions. The instructions are preferably executed by computer-executable components preferably integrated with the system 300 and one or more portions of the processor and/or a controller. The computer-readable medium can be stored on any suitable computer-readable media such as RAMs, ROMs, flash memory, EEPROMs, optical devices (CD or DVD), hard drives, floppy drives, or any suitable device. The computer-executable component is preferably a general or application specific processor, but any suitable dedicated hardware or hardware/firmware combination device can alternatively or additionally execute the instructions.

The FIGURES illustrate the architecture, functionality and operation of possible implementations of systems, methods and computer program products according to preferred embodiments, example configurations, and variations thereof. In this regard, each block in the flowchart or block diagrams may represent a module, segment, or portion of code, which comprises one or more executable instructions for implementing the specified logical function(s). It should also be noted that, in some alternative implementations, the functions noted in the block can occur out of the order noted in the FIGURES. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

As a person skilled in the field of biosignals will recognize from the previous detailed description and from the figures and claims, modifications and changes can be made to the preferred embodiments of the invention without departing from the scope of this invention defined in the following claims.

I claim:

1. A method for predicting spatial and temporal distributions of therapeutic substance carriers within a body, comprising:
    at a computing system, receiving an image dataset and a spectra dataset of a drug carrier;
    at the computing system, transforming the image dataset and the spectra dataset into a set of characteristics, wherein the set of characteristics comprises electrotopological characteristics, connectivity characteristics, molecular characteristics, and geometrical characteristics;
    generating a set of descriptors based upon the set of characteristics and a set of encoding functions;
    at the computing system, transforming the set of descriptors into a set of pharmacokinetic parameters and a set of pharmacodynamic parameters for the therapeutic substance carrier based upon a transformation model;
    at the computing system, transforming the set of pharmacokinetic parameters and the set of pharmacodynamic parameters into a spatial distribution and a temporal profile of the therapeutic substance carrier based upon a predictive model; and
    mapping the spatial distribution and the temporal profile onto at least a portion of an organ system of the user, thereby characterizing at least one of a concentration of the therapeutic substance carrier and a concentration of a therapeutic substance carried by the drug carrier in the organ system within a time window.

2. The method of claim 1, wherein receiving the image dataset and the spectra dataset comprises receiving the electron microscopy data from an electron microscopy module and receiving spectra data from at least one of an FTIR spectroscopy module, an NMR spectroscopy module, and an MS module.

3. The method of claim 1, wherein transforming the image dataset and the spectra dataset into the set of characteristics comprises generating electrotopological characteristics derived from molecular electrotopological state values of the therapeutic substance carrier, connectivity characteristics comprising chi indices of the therapeutic substance carrier, characteristics of molecular groups of the therapeutic substance carrier, and displacement moments along an inertial axis for the therapeutic substance carrier.

4. The method of claim 3, wherein transforming the image dataset and the spectra dataset into the set of characteristics comprises at least one of improving edge fidelity of an object captured within the image dataset and estimating motion behavior of a portion of the object captured within the image dataset.

5. The method of claim 1, wherein generating the set of descriptors based upon the set of characteristics and the set of encoding functions comprises processing the set of characteristics using at least one of a 2D autocorrelation function, a 3D autocorrelation function, and a radial distribution function.

6. The method of claim 1, wherein transforming the set of descriptors into the set of pharmacokinetic parameters and the set of pharmacodynamic parameters for the therapeutic substance carrier comprises generating values of a volume of distribution of a dose of the therapeutic substance, an unbound volume of distribution of the dose, a clearance of the therapeutic substance carrier from the body, and a half-life of the therapeutic substance carrier based upon the transformation model.

7. The method of claim 1, wherein mapping the spatial distribution and the temporal profile onto at least a portion of the organ system of the user comprises generating a model of the organ system of the user divided into a set of elements, and attributing an intensity value, corresponding to the concentration of the therapeutic substance carrier, to each of the set of elements based upon the spatial distribution and the temporal profile of the drug carrier.

8. A method for predicting spatial and temporal distributions of therapeutic substance carriers within a body of a user, comprising:
  at a computing system, receiving an image dataset and a spectra dataset of a therapeutic substance carrier generated from at least one of an imaging module and a spectra-generating module;
  at the computing system, transforming the image dataset and the spectra dataset into a set of characteristics, wherein the set of characteristics comprises electrotopological characteristics and geometrical characteristics;
  at the computing system, generating a set of pharmacokinetic parameters and a set of pharmacodynamic parameters for the therapeutic substance carrier based upon the set of characteristics and a transformation model; and
  at the computing system, transforming the set of pharmacokinetic parameters and the set of pharmacodynamic parameters into a spatial distribution and a temporal profile of the therapeutic substance carrier, based upon a predictive model incorporating physiological parameters of the body, thereby predicting distributions of the therapeutic substance carrier within the body.

9. The method of claim 8, wherein receiving the image dataset and the spectra dataset comprises receiving the electron microscopy data from an electron microscopy module and receiving spectra data from at least one of an FTIR spectroscopy module, an NMR spectroscopy module, and an mass spectroscopy module.

10. The method of claim 8, wherein transforming the image dataset and the spectra dataset into a set of characteristics further comprises generating connectivity characteristics and molecular characteristics of the therapeutic substance carrier.

11. The method of claim 10, wherein transforming the image dataset and the spectra dataset into the set of characteristics comprises generating electrotopological characteristics derived from molecular electrotopological state values of the therapeutic substance carrier, connectivity characteristics comprising chi indices of the therapeutic substance carrier, characteristics of molecular groups of the therapeutic substance carrier, and displacement moments along an inertial axis for the therapeutic substance carrier.

12. The method of claim 8, wherein generating the set of pharmacokinetic parameters and the set of pharmacodynamic parameters comprises generating a set of descriptors based upon processing the set of characteristics with a set encoding functions comprising at least one of a 2D autocorrelation function, a 3D autocorrelation function, and a radial distribution function.

13. The method of claim 12, wherein generating the set of descriptors comprises generating scalar descriptors comprising at least one of molecular weight, number of hydrogen bonding acceptors, topological polar surface area, and total charge of the therapeutic substance carrier.

14. The method of claim 12, further comprising transforming the set of descriptors into the set of pharmacokinetic parameters and the set of pharmacodynamic parameters, wherein transforming comprises generating values of a volume of distribution of a dose of the therapeutic substance, an unbound volume of distribution of the dose, a clearance of the therapeutic substance carrier from the body, and a half-life of the therapeutic substance carrier based upon the transformation model.

15. The method of claim 8, wherein transforming the set of pharmacokinetic parameters and the set of pharmacodynamic parameters into the temporal profile of the therapeutic substance carrier comprises processing the set of pharmacokinetic parameters and the set of pharmacodynamic parameters with a probabilistic model that determines an amount of the therapeutic substance carrier within a time window.

16. The method of claim 8, further comprising mapping the spatial distribution and the temporal profile onto an organ system of the user and generating a rendering of the mapping, thereby characterizing at least one of a concentration of the therapeutic substance carrier and a concentration of a therapeutic substance carried by the therapeutic substance carrier in the organ system within a time window.

17. The method of claim 8, further comprising training the transformation model based upon boosting and bootstrapped aggregation using training data characterizing at least one of drug carriers, drugs, and nanoparticles.

18. The method of claim 16, wherein mapping the spatial distribution and the temporal profile onto at least a portion of the organ system of the user comprises generating a model of the organ system of the user divided into a set of elements, and attributing an intensity value, corresponding to the concentration of the therapeutic substance carrier, to each of the set of elements based upon the spatial distribution and the temporal profile of the drug carrier.

19. A method for predicting distributions of therapeutic substance carriers within a body, comprising:
  at a computing system, receiving a dataset of a therapeutic substance carrier generated from at least one of an imaging module and a spectra-generating module;
  at the computing system, transforming the dataset into a set of characteristics, wherein the set of characteristics comprises at least one of electrotopological characteristics and geometrical characteristics;
  at the computing system, generating a set of parameters for the therapeutic substance carrier based upon the set of characteristics and a transformation model; and
  at the computing system, transforming the set of parameters into a spatial distribution and a temporal profile of the therapeutic substance carrier based upon a predictive module incorporating physiological parameters of the body, thereby predicting distributions of the therapeutic substance carrier within the body.

20. The method of claim 19, wherein transforming the dataset into the set of characteristics comprises generating electrotopological characteristics derived from molecular electrotopological state values of the therapeutic substance carrier, connectivity characteristics comprising chi indices of the therapeutic substance carrier, characteristics of molecular groups of the therapeutic substance carrier, and displacement moments along an inertial axis for the therapeutic substance carrier.

* * * * *